(12) United States Patent
Serfati

(10) Patent No.: US 10,576,200 B1
(45) Date of Patent: Mar. 3, 2020

(54) STERILE FILTERED LUER SLIP IV SET FOR SERUM BOTTLE HIGH VOLUME INFUSION FOR VETERINARY USE

(71) Applicant: Biogalenic, LLC., Aventura, FL (US)

(72) Inventor: Jacob Serfati, Aventura, FL (US)

(73) Assignee: BIOGALENIC, LLC., Aventura, FL (US)

( * ) Notice: Subject to any disclaimer, the term of this patent is extended or adjusted under 35 U.S.C. 154(b) by 128 days.

(21) Appl. No.: 15/730,236

(22) Filed: Oct. 11, 2017

(51) Int. Cl.
*A61M 5/162* (2006.01)
*A61D 7/00* (2006.01)
*A61M 5/165* (2006.01)

(52) U.S. Cl.
CPC ............. *A61M 5/162* (2013.01); *A61D 7/00* (2013.01); *A61M 5/165* (2013.01)

(58) Field of Classification Search
CPC .. A61M 2005/1623; A61M 2039/0036; A61M 2039/205; A61M 5/162
See application file for complete search history.

(56) References Cited

U.S. PATENT DOCUMENTS

| | | | | | |
|---|---|---|---|---|---|
| 2,770,234 | A | * | 11/1956 | Nesset | A61M 5/162 215/261 |
| 3,484,849 | A | * | 12/1969 | Maenz | A61J 1/2089 137/575 |
| 4,998,926 | A | * | 3/1991 | Alchas | A61M 5/14 604/251 |
| 2009/0159485 | A1 | * | 6/2009 | Jakob | A61M 5/162 206/571 |

* cited by examiner

*Primary Examiner* — Nathan R Price
*Assistant Examiner* — Melissa A Snyder
(74) *Attorney, Agent, or Firm* — Albert Bordas, P.A.

(57) ABSTRACT

A sterile filtered luer slip iv set for serum bottle high volume infusion for veterinary use, having a luer fitting assembly that has an air inlet connective tube connected to an air valve assembly, which has a filter. The luer fitting assembly fits into a mouth of a bottle and connects to a connector assembly for veterinary use infusions. The luer fitting assembly has a tubing connector sidewall, and a base sidewall having an air inlet face, which has an air inlet. The luer fitting assembly further has a flange and an insert sidewall. The air inlet connective tube extends from the interior base wall to the insert edge and aligns with the air inlet to allow air to enter via the air inlet through the air inlet connective tube and the filter, reaching an interior of the bottle.

13 Claims, 4 Drawing Sheets

US 10,576,200 B1

STERILE FILTERED LUER SLIP IV SET FOR SERUM BOTTLE HIGH VOLUME INFUSION FOR VETERINARY USE

BACKGROUND OF THE INVENTION

1. Field of the Invention

The present invention relates to luer slip IV sets, and more particularly, to sterile filtered luer slip IV sets for use with serum bottles during veterinary use high volume infusions.

2. Description of the Related Art

Contamination of sterile solutions during infusion is a concern. Applicant is not aware of any prior art suggesting the novel features of the present invention.

SUMMARY OF THE INVENTION

The present invention is a sterile filtered luer slip iv set for serum bottle high volume infusion for veterinary use, comprising a luer fitting assembly which has an air inlet connective tube connected to an air valve assembly comprising a filter, wherein the luer fitting assembly fits into a mouth of a bottle and connects to a connector assembly for veterinary use infusions.

The luer fitting assembly comprises a tubing connector sidewall having first and second ends, and a tubing connector cavity defined by the tubing connector sidewall. The luer fitting assembly further comprises a base sidewall with a base flange end and an air inlet face having an air inlet. The air inlet face is defined by an air inlet face perimeter. The tubing connector sidewall extends from the air inlet face. The base sidewall extends approximately centered from a flange. The luer fitting assembly further comprises an insert sidewall having an insert end and an insert edge. The flange is positioned between the insert sidewall and the base sidewall. The insert sidewall defines a cavity with an interior base wall. The air inlet connective tube extends from the interior base wall to the insert edge and protrudes from an interior side of the insert sidewall. The tubing connector cavity extends between the insert edge and the interior base wall. The base sidewall has a first predetermined diameter and the insert sidewall has a second predetermined diameter, wherein the second predetermined diameter is larger than the first predetermined diameter.

The air valve assembly comprises a head having the filter. Extending from the head is an air valve sidewall that defines a lip. The air valve assembly is secured onto the air inlet connective tube, and the head extends from the insert edge.

The connector assembly comprises a connective tube secured within the first end. At least a section of the insert sidewall is inserted into the mouth. The air inlet connective tube aligns with the air inlet to allow air to enter via the air inlet through the air inlet connective tube and the filter, reaching an interior of the bottle.

It is therefore one of the main objects of the present invention to provide a luer slip IV set.

It is another object of this invention to provide a sterile filtered luer slip IV set for serum bottle high volume infusion for veterinary use.

It is another object of this invention to provide a sterile filtered luer slip IV set for serum bottle high volume infusion for veterinary use, which has an air valve assembly.

It is another object of this invention to provide a sterile filtered luer slip IV set for serum bottle high volume infusion for veterinary use, which is of a durable and reliable construction.

It is yet another object of this invention to provide such a sterile filtered luer slip IV set for serum bottle high volume infusion for veterinary use that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
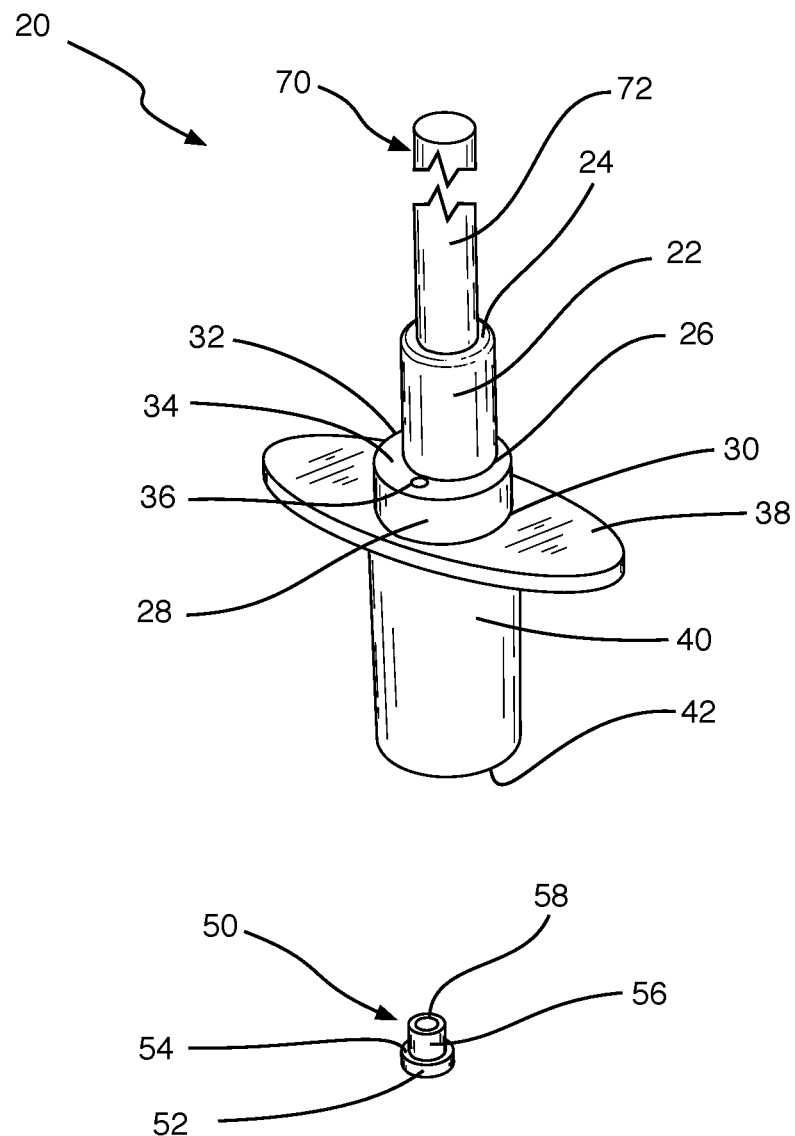
FIG. 1 represents an isometric view of a valve assembly removed from a luer fitting assembly of the present invention.

Referring now to the drawings, the present invention is a sterile filtered luer slip IV set for serum bottle high volume infusion for veterinary use, and is generally referred to with numeral 10. It is noted that "IV" means intravenous, defined as: 1) into a vein. Intravenous medications are solutions administered directly into the venous circulation via a syringe or intravenous catheter (tube); 2) the actual solution that is administered intravenously; and 3) the device used to administer an intravenous solution, such as an IV drip. It can be observed that it basically includes luer fitting assembly 20 and air valve assembly 50.

As seen in FIG. 1, luer fitting assembly 20 comprises tubing connector sidewall 22 having first and second ends 24 and 26. Connector assembly 70 comprises connective tube 72, a section being illustrated, that is connected to tubing connector sidewall 22 through end 24. Luer fitting assembly 20 further comprises base sidewall 28, which has base flange end 30, and air inlet face 34. Air inlet face 34 defines air inlet face perimeter 32. Tubing connector sidewall 22 extends from air inlet face 34 and is relatively displaced toward one side of air inlet face perimeter 32. Base sidewall 28 extends from flange 38, which is positioned approximately centered between base sidewall 28 and insert sidewall 40.

Air valve assembly 50 comprises head 52 and air valve edge 58. Air valve sidewall 56 extends from head 52 to valve edge 58 defining lip 54.

Figure 2:
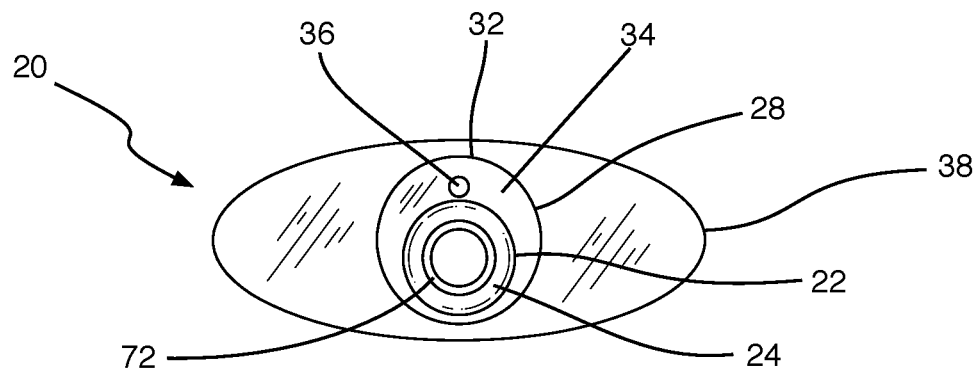
FIG. 2 is a bottom view of the luer fitting assembly of the present invention.
Figure 4:
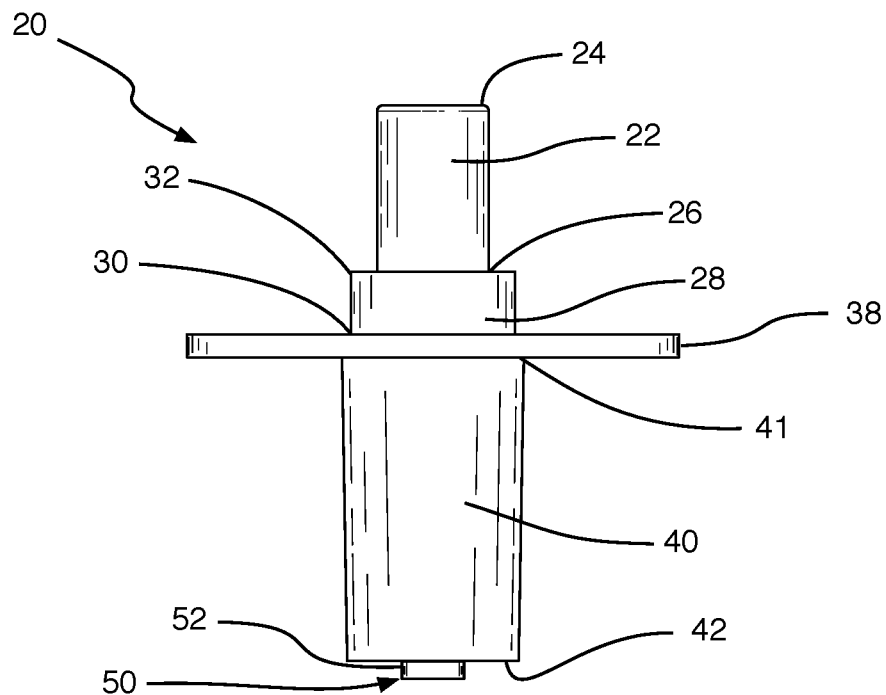
FIG. 4 is a front view of the valve assembly mounted onto the luer fitting assembly of the present invention.

As seen in FIG. 2, flange 38 is oval in shape. Base sidewall 28 is approximately centered positioned onto flange 38. Air inlet face 34 comprises air inlet 36, which allows for air, such as but not limited to ambient air, to enter into luer fitting assembly 20. It is noted that the air enters without non-sterile particles, whereby filter 51 prevents non-sterile particles from passing therethrough. Connective tube 72 is connected, or inserted into first end 24 of tubing connector sidewall 22, whereby tubing connector cavity 23, seen in FIG. 3, receives connective tube 72.

Figure 3:
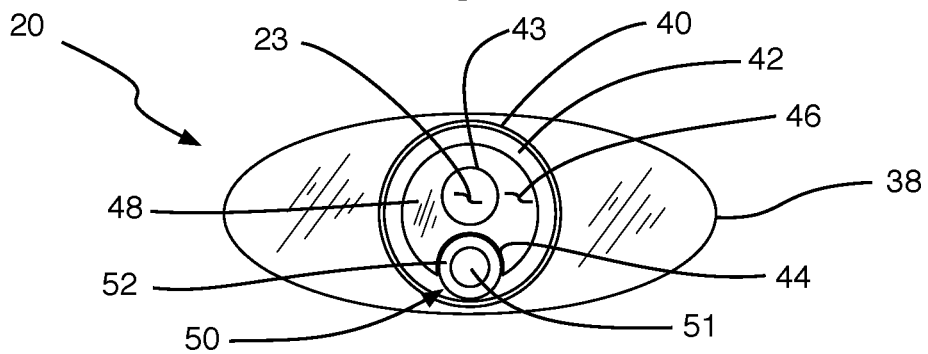
FIG. 3 is a top view of the valve assembly mounted onto the luer fitting assembly of the present invention.
Figure 5:
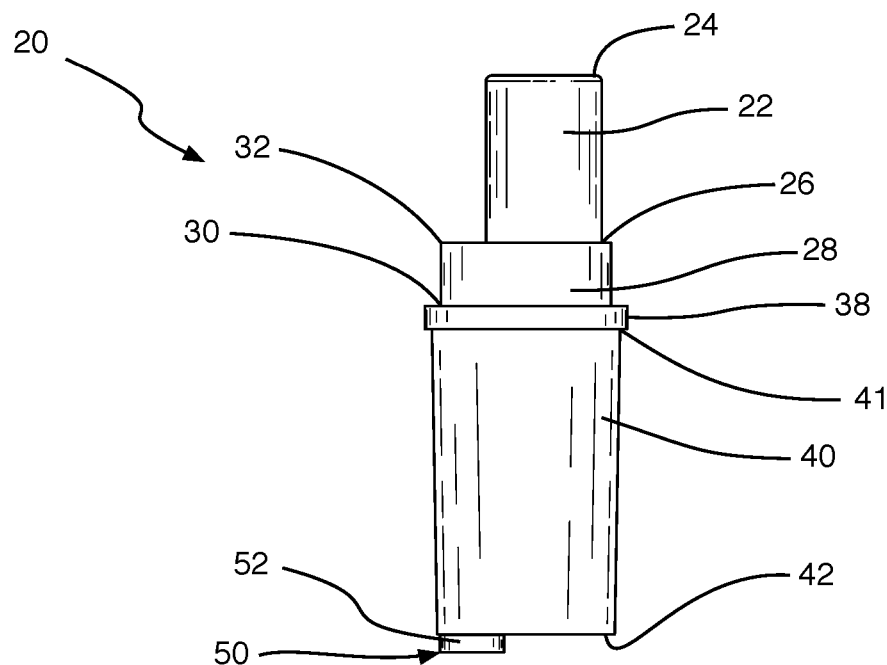
FIG. 5 is a right side view of the valve assembly mounted onto the luer fitting assembly of the present invention.
Figure 6:
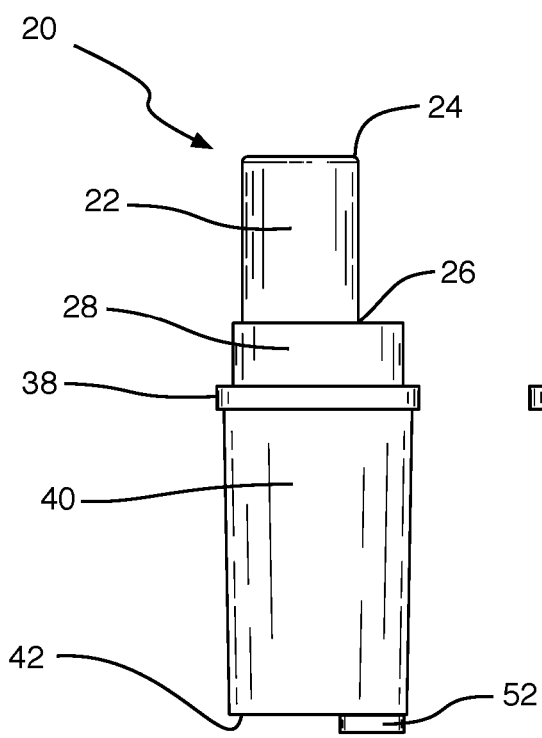
FIG. 6 is a left side view of the valve assembly mounted onto the luer fitting assembly of the present invention.
Figure 7:
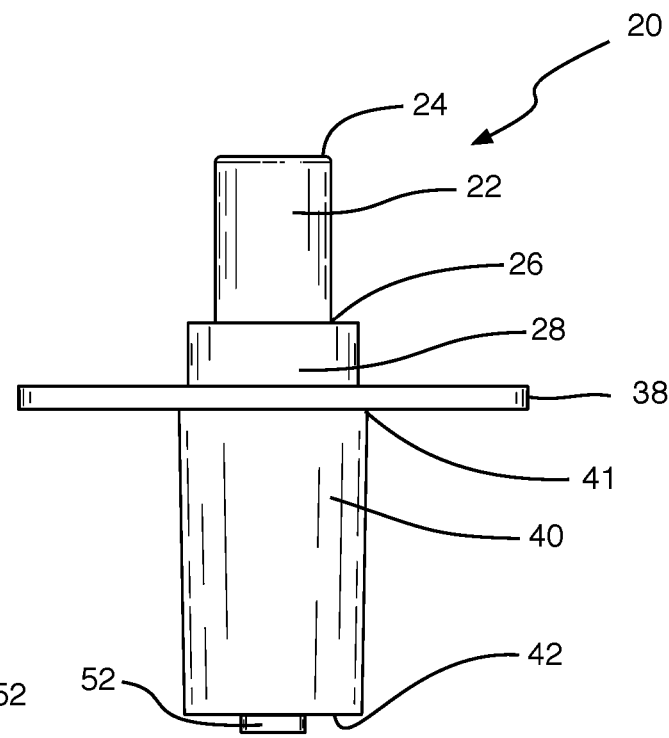
FIG. 7 is a rear view of the valve assembly mounted onto the luer fitting assembly of the present invention.

As seen in FIG. 3, insert sidewall 40 and interior base wall 48 define cavity 46. Interior base wall 48 has interior insert edge 43. Tubing connector sidewall 22, seen in FIG. 1, defines tubing connector cavity 23 that extends to interior insert edge 43 at interior base wall 48. Liquid matter flows through tubing connector cavity 23. Insert sidewall 40 comprises air inlet connective tube 44, which extends from interior base wall 48 to insert edge 42. Air inlet connective tube 44 protrudes from an interior side of insert sidewall 40. Air valve assembly 50 comprises filter 51, whereby head 52 secures filter 51.

As seen in FIGS. 4, 5, 6, and 7, insert sidewall 40 has insert end 41 and insert edge 42. Base sidewall 28 has a first predetermined diameter and insert sidewall 40 has a second predetermined diameter, wherein the second predetermined diameter is slightly larger than the first predetermined diameter. Air valve assembly 50 is connected onto air inlet connective tube 44 seen in FIG. 3, whereby head 52 extends from insert edge 42.

Figure 8:
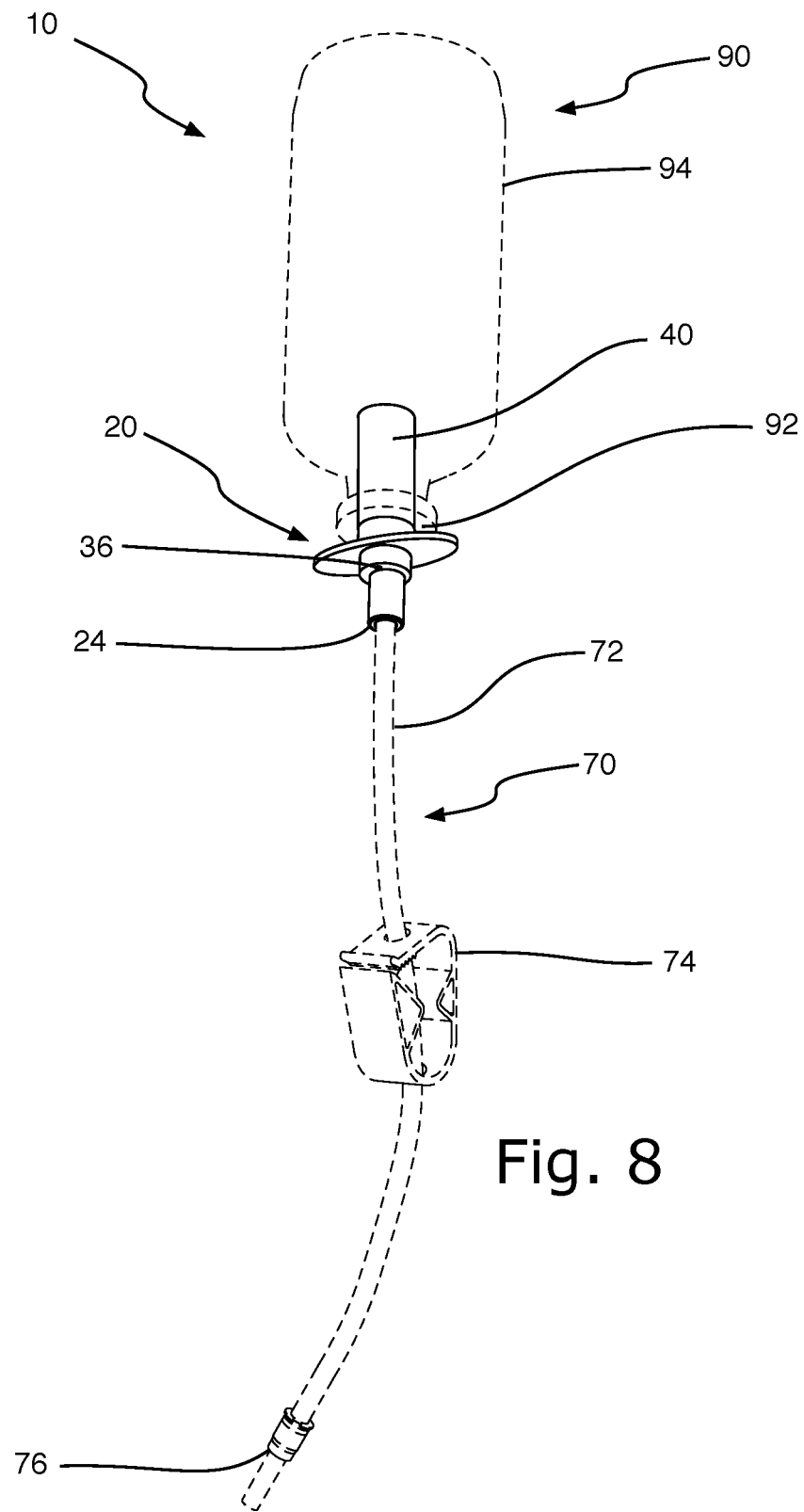
FIG. 8 is an isometric view of the present invention.

As seen in FIG. 8, bottle 90 comprises mouth 92 and sidewall 94. Connector assembly 70 comprises clamp 74 and fitting 76 coupled to connective tube 72. Luer fitting assembly 20 is connected to bottle 90, whereby at least a section of insert sidewall 40 is inserted into mouth 92, and connective tube 72 is connected into first end 24, allowing liquid matter to flow from bottle 90 through luer fitting assembly 20 and connective tube 72. Air inlet connective tube 44 aligns with air inlet 36 to allow air to enter via air inlet 36, through air inlet connective tube 44 and filter 51, seen in FIG. 3, to reach an interior of bottle 90. This allows the liquid matter to easy flow from bottle 90 thereout.

Bottle 90 may contain any liquid matter to be administered during a veterinarian procedure, such as, but not limited to, sodium chloride solutions, dextrose solutions, and/or any other pharmacologic solutions including medications. In one embodiment, liquid matter comprises a solution containing sodium chloride, sodium lactate, potassium chloride, and calcium chloride. In another embodiment, liquid matter comprises pharmacologic solutions such as analgesics, anesthesia, anti-inflammatories, antibiotics, vitamins, supplements, and/or any medications.

In a preferred embodiment, present invention 10 is packaged in sterile packaging. Present invention 10 does not contaminate the liquid matter, which is a sterile solution that is infused intravenously from bottle 90. More specifically, present invention 10 prevents contamination of the liquid matter by preventing non-sterile particles from contacting the liquid matter during infusion. Furthermore, filter 51 cleans the air that contacts the liquid matter infused intravenously to a patient to prevent contamination of the liquid matter.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A sterile filtered luer slip iv set for serum bottle high volume infusion for veterinary use, comprising:
A) a luer fitting assembly comprising a tubing connector sidewall having a proximal end and a distal end, said luer fitting assembly further comprises a base sidewall, which has a base flange end, and an air inlet face, said air inlet face defines an air inlet face perimeter at said proximal end, said air inlet face comprises an air inlet, which allows for air to enter into said luer fitting assembly, said tubing connector sidewall extends from said air inlet face and is relatively displaced toward one side of said air inlet face perimeter, said base sidewall extends from a flange, which is positioned approximately centered between a base sidewall and an insert sidewall having a distal insert edge, whereby extending in a first direction from said flange is said insert wall having said distal insert edge, and extending from said flange in a second direction that is opposite to said first direction is said base sidewall that extends to said air inlet face, and extending from said air inlet face is said tubing connector sidewall having said distal end, and a connector assembly comprises a connective tube that is connected to said tubing connector sidewall through said distal end, said connective tube is inserted into said distal end of said tubing connector sidewall, further comprising a tubing connector cavity for receiving said connective tube, said luer fitting assembly further comprising an interior base wall having an interior insert edge, said tubing connector sidewall defines said tubing connector cavity that extends to said interior insert edge at said interior base wall, liquid matter flows through said tubing connector cavity, said insert sidewall and said interior base wall define a cavity, said insert sidewall comprising an air inlet connective tube, which extends from said interior base wall to an insert edge, and said air inlet connective tube protrudes from an interior side of said insert sidewall; and
B) an air valve assembly comprising a proximal head, a distal air valve edge, a filter, and an air valve sidewall that extends from said proximal head to said distal valve edge to define a lip, said air valve assembly is connected onto said air inlet connective tube of said luer fitting assembly, whereby said proximal head extends from said distal insert edge.

2. The sterile filtered luer slip iv set for serum bottle high volume infusion for veterinary use set forth in claim 1, further characterized in that said head secures said filter.

3. The sterile filtered luer slip iv set for serum bottle high volume infusion for veterinary use set forth in claim 2, further characterized in that said insert sidewall has an insert end and said insert edge.

4. The sterile filtered luer slip iv set for serum bottle high volume infusion for veterinary use set forth in claim 3, further characterized in that said base sidewall has a first predetermined diameter and said insert sidewall has a second predetermined diameter, wherein the second predetermined diameter is larger than the first predetermined diameter.

5. The sterile filtered luer slip iv set for serum bottle high volume infusion for veterinary use set forth in claim 4, further comprising a bottle having a mouth and a sidewall, and said connector assembly comprising a clamp and a fitting coupled to said connective tube, whereby said luer fitting assembly is connected to said bottle and at least a section of said insert sidewall is inserted into said mouth, and said connective tube is connected into said distal end, allowing said liquid matter to flow from said bottle through said luer fitting assembly and said connective tube.

6. The sterile filtered luer slip iv set for serum bottle high volume infusion for veterinary use set forth in claim 5, further characterized in that said air inlet connective tube aligns with said air inlet to allow air to enter said via air inlet, through said air inlet connective tube and said filter to reach an interior of said bottle and allow said liquid matter to flow from said bottle there out.

7. The sterile filtered luer slip iv set for serum bottle high volume infusion for veterinary use set forth in claim 6, further characterized in that said bottle contains said liquid matter to be administered during a veterinarian procedure.

8. The sterile filtered luer slip iv set for serum bottle high volume infusion for veterinary use set forth in claim 7, further characterized in that said liquid matter is sodium chloride solutions, dextrose solutions, and/or pharmacologic solutions including medications.

9. The sterile filtered luer slip iv set for serum bottle high volume infusion for veterinary use set forth in claim 7, further characterized in that said liquid matter comprises a solution containing sodium chloride, sodium lactate, potassium chloride, and calcium chloride.

10. The sterile filtered luer slip iv set for serum bottle high volume infusion for veterinary use set forth in claim 7, further characterized in that said liquid matter comprises pharmacologic solutions including analgesics, anesthesia, anti-inflammatories, antibiotics, vitamins, supplements, and/or medications.

11. The sterile filtered luer slip iv set for serum bottle high volume infusion for veterinary use set forth in claim 7, prevents contamination of said liquid matter by preventing non-sterile particles from contacting said liquid matter during an infusion.

12. The sterile filtered luer slip iv set for serum bottle high volume infusion for veterinary use set forth in claim 7, further characterized in that said filter cleans air that contacts said liquid matter infused intravenously to a patient to prevent contamination of said liquid matter.

13. The sterile filtered luer slip iv set for serum bottle high volume infusion for veterinary use set forth in claim 7, further characterized in that said flange is oval in shape and said base sidewall is approximately centered positioned onto said flange.

* * * * *